(12) United States Patent  
Wolf et al.

(10) Patent No.: US 7,705,974 B2  
(45) Date of Patent: Apr. 27, 2010

(54) METROLOGY SYSTEM WITH SPECTROSCOPIC ELLIPSOMETER AND PHOTOACOUSTIC MEASUREMENTS

(75) Inventors: Robert Gregory Wolf, Hackettstown, NJ (US); Christopher Morath, Morristown, NJ (US); Robin Mair, Wintersprings, FL (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 12/381,477

(22) Filed: Mar. 11, 2009

(65) Prior Publication Data

US 2009/0201502 A1    Aug. 13, 2009

Related U.S. Application Data

(60) Division of application No. 11/881,079, filed on Jul. 24, 2007, now Pat. No. 7,522,272, which is a continuation of application No. 11/343,717, filed on Jan. 30, 2006, now Pat. No. 7,253,887, which is a continuation of application No. 10/193,769, filed on Jul. 10, 2002, now Pat. No. 7,006,221.

(60) Provisional application No. 60/305,227, filed on Jul. 13, 2001, provisional application No. 60/306,120, filed on Jul. 17, 2001.

(51) Int. Cl.  
*G01N 21/00* (2006.01)

(52) U.S. Cl. ............................ 356/73; 356/630; 356/369

(58) Field of Classification Search ............. 356/72–73, 356/369, 630  
See application file for complete search history.

(56) References Cited

U.S. PATENT DOCUMENTS

| | | | |
|---|---|---|---|
| 5,329,357 A | 7/1994 | Bernoux et al. | 356/369 |
| 5,402,237 A | 3/1995 | Rhiger et al. | 356/369 |
| 5,748,318 A | 5/1998 | Maris et al. | 356/381 |
| 5,900,939 A | 5/1999 | Aspnes et al. | 356/369 |
| 5,910,842 A | 6/1999 | Piwonka-Corle et al. | 356/369 |
| 5,959,735 A | 9/1999 | Maris et al. | 356/381 |
| 5,973,787 A | 10/1999 | Aspnes et al. | 356/369 |
| 5,978,074 A | 11/1999 | Opsal et al. | 356/72 |
| 6,008,906 A | 12/1999 | Maris | 356/432 |
| 6,052,188 A | 4/2000 | Fluckiger et al. | 356/369 |
| 6,069,703 A | 5/2000 | Banet et al. | 356/432 |
| 6,320,666 B1 * | 11/2001 | Opsal et al. | 356/369 |
| 6,633,831 B2 | 10/2003 | Nikoonahad et al. | 702/155 |
| 6,673,637 B2 | 1/2004 | Wack et al. | 438/14 |
| 6,694,284 B1 | 2/2004 | Nikoonahad et al. | 702/155 |

(Continued)

OTHER PUBLICATIONS

Duggal, Anil R., et al, "Real-time optical characterization of surface acoustic modes of polymide thin-film coatings", Oct. 1, 1992, Journal of Applied Physics, vol. 72, No. 7, pp. 2823-2839.

*Primary Examiner*—Kara E Geisel  
(74) *Attorney, Agent, or Firm*—Harrington & Smith

(57) ABSTRACT

An optical system includes both a microspot broadband spectroscopic ellipsometer and a photoacoustic film thickness measurement system that are supplied laser light by the same laser light source. One of the systems makes a measurement, the result of which is used to adjust a parameter of the other system; e.g. the ellipsometer measures thickness and the photoacoustic system uses the thickness result to measure the speed of sound. In one version, the ellipsometer converts the laser beam to a broad-spectrum beam that provides higher intensity.

16 Claims, 8 Drawing Sheets

U.S. PATENT DOCUMENTS

| | | | |
|---|---|---|---|
| 6,782,337 B2 | 8/2004 | Wack et al. | 702/155 |
| 6,806,951 B2 | 10/2004 | Wack et al. | 356/237.2 |
| 6,812,045 B1 | 11/2004 | Nikoonahad et al. | 438/14 |
| 6,818,459 B2 | 11/2004 | Wack et al. | 438/14 |
| 6,829,559 B2 | 12/2004 | Bultman et al. | 702/155 |
| 2002/0028044 A1 | 3/2002 | Birk et al. | 385/43 |
| 2002/0044346 A1 | 4/2002 | Nguyen et al. | 359/368 |
| 2002/0097406 A1* | 7/2002 | Fielden et al. | 356/630 |
| 2002/0163634 A1* | 11/2002 | Meeks et al. | 356/73 |
| 2004/0035529 A1 | 2/2004 | Grimbergen | 438/16 |

* cited by examiner

METROLOGY SYSTEM WITH SPECTROSCOPIC ELLIPSOMETER AND PHOTOACOUSTIC MEASUREMENTS

PRIORITY CLAIM AND CROSS-REFERENCE TO RELATED PATENT APPLICATIONS

This patent application is a divisional application of U.S. patent application Ser. No. 11/881,079 (filed Jul. 24, 2007) now U.S. Pat. No. 7,522,272 which is a continuation of U.S. patent application Ser. No. 11/343,717 (filed Jan. 30, 2006, now issued as U.S. Pat. No. 7,253,887), which is itself a continuation of U.S. patent application Ser. No. 10/193,769 (filed Jul. 10, 2002, now issued as U.S. Pat. No. 7,006,221). The latter application claims priority to Provisional U.S. Patent Application No. 60/305,277 (filed Jul. 13, 2001) and Provisional U.S. Patent Application No. 60/306,120 (filed Jul. 17, 2001). Each and every one of the above-cited applications is incorporated by reference herein in their entireties, and priority is hereby claimed to each of them through the above chain.

BACKGROUND OF THE INVENTION

The semiconductor processing industry has made significant progress in recent years in forming ever-smaller minimum device geometries, which has created a need for processes that form very thin films. This development has in turn led to a need for metrology equipment to measure those films. In many process steps, the thickness of the thin films used to form these structures is becoming ever thinner. Gate oxide thicknesses, for example are now typically on the order of 10 to 20 Angstroms thick. One technique for measuring the thickness of such films is known as ellipsometry.

Ellipsometry is a non-contact, nondestructive, optical technique for the characterization of transparent thin films on surfaces. When a surface or interface is struck by polarized light, ellipsometers measure the change in the reflected light's polarization by detecting and quantifying the change in the amplitude ratio (psi) and the change in phase (delta) induced by reflection of light from the surface.

In another trend, the increasing requirements of high-speed and low-power semiconductor devices has resulted in a significant shift away from aluminum conductors and silicon oxide insulators as the dominant metal/insulator combination in semiconductor multi-level metallization technology. Copper and low k dielectric materials are replacing aluminum metallurgy and silicon oxide dielectrics. It is also anticipated that copper metallurgy and low k dielectric materials will dominate the semiconductor integrated circuit designs. One technique for measuring the thickness of metal films is known as photoacoustic film thickness measurement.

Photoacoustic film thickness measurement is a non-contact, nondestructive optical technique for measuring the thickness of single or multi-layer opaque metal films. A photoacoustic thickness measurement system forms two optical beams: an excitation beam used to excite the surface of the film sample periodically, and a probe beam used to sense the reflectivity of the surface of the sample following each pulse from the excitation beam.

PRIOR ART

Prior Art for Photoacoustic Film Thickness Measurement

U.S. Pat. No. 6,069,703 entitled "Method and device for simultaneously measuring the thickness of multiple thin metal films in a multilayer structure", assigned to Active Impulse Systems, Inc., (Natick, Mass.), discloses an apparatus for measuring a property of a structure comprising at least one layer, the apparatus including a light source that produces an optical pulse having a duration of less than 10 ps; a diffractive element that receives the optical pulse and diffracts it to generate at least two excitation pulses; an optical system that spatially and temporally overlaps at least two excitation pulses on or in the structure to form an excitation pattern, containing at least two light regions, that launches an acoustic wave having an out-of-plane component that propagates through the layer, reflects off a lower boundary of the layer, and returns to a surface of the structure to modulate a property of the structure; a light source that produces a probe pulse that diffracts off the modulated property to generate at least one signal pulse; a detector that receives at least one signal pulse and in response generates a light-induced electrical signal; and an analyzer that analyzes the light-induced electrical signal to measure the property of the structure.

U.S. Pat. No. 6,008,906 entitled "Optical method for the characterization of the electrical properties of semiconductors and insulating films", assigned to Brown University Research Foundation, (Providence, R.I.), discloses a method for characterizing a sample including the steps of (a) providing a semiconductor material; (b) applying at least one of an electric field, a pulsed or cw light source, a change in temperature and/or a change in pump pulse intensity to the semiconductor material; (c) absorbing pump light pulses in a portion of the semiconductor material and measuring changes in optical constants as indicated by probe light pulses applied at some time t following the absorption of the pump light pulses; and (e) associating a measured change in the optical constants with at least one of a surface charge, dopant concentration, trap density, or minority carrier lifetime.

U.S. Pat. No. 5,959,735 entitled "Optical stress generator and detector," assigned to Brown University Research Foundation, (Providence, R.I.), discloses a system for the characterization of thin films and interfaces between thin films through measurements of their mechanical and thermal properties. In the system, light is absorbed in a thin film or in a structure made up of several thin films, and the change in optical transmission or reflection is measured and analyzed. The change in reflection or transmission is used to give information about the ultrasonic waves that are produced in the structure. The information that is obtained from the use of the measurement methods and apparatus of this invention can include: (a) a determination of the thickness of thin films with a speed and accuracy that is improved compared to earlier methods; (b) a determination of the thermal, elastic, and optical properties of thin films; (c) a determination of the stress in thin films; and (d) a characterization of the properties of interfaces, including the presence of roughness and defects.

U.S. Pat. No. 5,748,318 entitled "Optical stress generator and detector," assigned to Brown University Research Foundation, (Providence, R.I.), discloses a system for the characterization of thin films and interfaces between thin films through measurements of their mechanical and thermal properties. In the system, light is absorbed in a thin film or in a structure made up of several thin films, and the change in optical transmission or reflection is measured and analyzed. The change in reflection or transmission is used to give information about the ultrasonic waves that are produced in the structure. The information that is obtained from the use of the measurement methods and apparatus of this invention can include: (a) a determination of the thickness of thin films with a speed and accuracy that is improved compared to earlier methods; (b) a determination of the thermal, elastic, and optical properties of thin films; (c) a determination of the stress in thin films; and (d) a characterization of the properties of interfaces, including the presence of roughness and defects.

Prior Art for Spectroscopic Ellipsometer

U.S. Pat. No. 5,978,074 entitled "Apparatus for evaluating metallized layers on semiconductors," assigned to Therma-Wave, Inc., (Fremont, Calif.), discloses an apparatus for characterizing multilayer samples. An intensity modulated pump beam is focused onto the sample surface to periodically excite the sample. A probe beam is focused onto the sample surface within the periodically excited area. The power of the reflected probe beam is measured by a photodetector. The output of the photodetector is filtered and processed to derive the modulated optical reflectivity of the sample. Measurements are taken at a plurality of pump beam modulation frequencies. In addition, measurements are taken as the lateral separation between the pump and probe beam spots on the sample surface is varied. The measurements at multiple modulation frequencies and at different lateral beam spot spacings are used to help characterize complex multilayer samples. In the preferred embodiment, a spectrometer is also included to provide additional data for characterizing the sample.

U.S. Pat. No. 5,973,787 entitled "Broadband spectroscopic rotating compensator ellipsometer," assigned to Therma-Wave, Inc., (Fremont, Calif.), discloses an ellipsometer, and a method of ellipsometry, for analyzing a sample using a broad range of wavelengths, including a light source for generating a beam of polychromatic light having a range of wavelengths of light for interacting with the sample. A polarizer polarizes the light beam before the light beam interacts with the sample. A rotating compensator induces phase retardations of a polarization state of the light beam wherein the range of wavelengths and the compensator are selected such that at least a first phase retardation value is induced that is within a primary range of effective retardations of substantially 135° to 225°, and at least a second phase retardation value is induced that is outside of the primary range. An analyzer interacts with the light beam after the light beam interacts with the sample. A detector measures the intensity of light after interacting with the analyzer as a function of compensator angle and of wavelength, preferably at all wavelengths simultaneously. A processor determines the polarization state of the beam as it impinges the analyzer from the light intensities measured by the detector.

U.S. Pat. No. 5,910,842 entitled "Focused beam spectroscopic ellipsometry method and system," assigned to KLA-Tencor Corporation, (San Jose, Calif.), discloses a method and system for spectroscopic ellipsometry employing reflective optics to measure a small region of a sample by reflecting radiation (preferably broadband UV, visible, and near infrared radiation) from the region. The system preferably has an autofocus assembly and a processor programmed to determine from the measurements the thickness and/or complex refractive index of a thin film on the sample. Preferably, only reflective optics are employed along the optical path between the polarizer and analyzer, a sample beam reflects with low incidence angle from each component of the reflective optics, the beam is reflectively focused to a small, compact spot on the sample at a range of high incidence angles, and an incidence angle selection element is provided for selecting for measurement only radiation reflected from the sample at a single, selected angle (or narrow range of angles). The focusing mirror preferably has an elliptical shape to reduce off-axis aberrations in the focused beam. Some embodiments include both a spectrophotometer and an ellipsometer integrated together as a single instrument. In such instrument, the spectrophotometer and ellipsometer share a radiation source, and radiation from the source can be focused by either the spectrophotometer or the ellipsometer to the same focal point on a sample. Preferred embodiments of the ellipsometer employ a rotating, minimal-length Rochon prism as a polarizer, and include a spectrometer with an intensified photodiode array to measure reflected radiation from the sample, and a reference channel (in addition to a sample channel which detects radiation reflected from the sample).

U.S. Pat. No. 5,900,939 entitled "Thin film optical measurement system and method with calibrating ellipsometer," assigned to Therma-Wave, Inc., (Fremont, Calif.), discloses an optical measurement system for evaluating a reference sample that has at least a partially known composition. The optical measurement system includes a reference ellipsometer and at least one non-contact optical measurement device. The reference ellipsometer includes a light generator, an analyzer and a detector. The light generator generates a beam of quasimonochromatic light having a known wavelength and a known polarization for interacting with the reference sample. The beam is directed at a non-normal angle of incidence relative to the reference sample to interact with the reference sample. The analyzer creates interference between the S and P polarized components in the light beam after the light beam has interacted with reference sample. The detector measures the intensity of the light beam after it has passed through the analyzer. A processor determines the polarization state of the light beam entering the analyzer from the intensity measured by the detector, and determines an optical property of the reference sample based upon the determined polarization state, the known wavelength of light from the light generator and the composition of the reference sample. The processor also operates the optical measurement device to measure an optical parameter of the reference sample. The processor calibrates the optical measurement device by comparing the measured optical parameter from the optical measurement device to the determined optical property from the reference ellipsometer.

U.S. Pat. No. 6,052,188 entitled "Spectroscopic ellipsometer," assigned to Verity Instruments, Inc., (Carrollton, Tex.), discloses a spectral ellipsometer that enables complete simultaneous measurement of ellipsometric parameters of a surface with thin films and coatings for the full wavelength range of interest by using an imaging spectrograph together with a novel optical arrangement that disperses the polarization information of a time-invariant train of optical signals in a linear spatial array of points along or parallel to an input aperture or slit of the imaging spectrograph and disperses the polarization information in wavelength perpendicular to the aperture or slit to provide a two-dimensional spectrograph image that is collected and stored by an imaging array with one axis relating to wavelength and the other axis relating to the light polarization. Multiple simultaneous measurements of the spectral ellipsometric parameters psi and delta are taken at all wavelengths without the need of any time-varying or mechanically-moving optical elements. The ellipsometer can be used for real-time measurements of ellipsometric parameters of a moving or static surface with the thin films and coatings.

U.S. Pat. No. 5,329,357 entitled "Spectroscopic ellipsometry apparatus including an optical fiber," assigned to Sopra-Societe De Production Et De Recherches Appliquees, (Bois-Colombes, FR), discloses a spectroscopic ellipsometer comprises a wideband light source, together with a first optical system including a rotating polarizer which applies a parallel beam to a sample contained in an enclosure. The reflected beam is picked up by an analyzer in a second optical system which transmits said reflected beam to a monochromator which is followed by a photodetector which is connected to control electronics connected, in turn, to a microcomputer. An optical fiber is provided between the source and the first optical system. Advantageously, a second optical fiber provided between the second optical system and the monochromator.

Since higher speed and higher precision thickness measurement boosts the throughput and yield of semiconductor processing lines, which in turn contribute significant economic benefit to semiconductor manufacturers, there is a strong demand for such improvements in the industry. Likewise, there is also a strong demand in the industry for systems with the flexibility to handle a broad range of measurement requirements.

Semiconductor device fabrication plants house numerous pieces of equipment, each having their own space requirements for installation. Since the space required by each piece of equipment in a plant contributes directly to the total overhead cost of the plant, it is desirable to reduce the total space requirement of a plant by combining and integrating the functions of multiple pieces of equipment into one piece of equipment.

In the field of metrology, ellipsometers measure the thickness of transparent films, and photoacoustic film thickness measurement systems measure the thickness of opaque films. However, these separate pieces of equipment each require their own installation space in a semiconductor fabrication plant, which leads to a high overhead cost of the plant. What is needed is a way to provide a dual system for measuring the thickness of transparent and opaque films.

SUMMARY OF THE INVENTION

The invention relates to a dual metrology system having both a spectroscopic ellipsometer and a photoacoustic film thickness measurement system.

A feature of the invention is that the spectroscopic ellipsometer and photoacoustic measurement system are supplied laser light by the same laser light source.

Another feature of the invention is that the spectroscopic ellipsometer is a microspot broadband spectroscopic ellipsometer.

Yet another feature of the present invention is a method of measuring the thickness of a film on a wafer comprising the steps of positioning in the measurement area a selected site on a film formed on a sample; using either the ellipsometer or photoacoustic system to make a measurement on the selected site; and using the result of that measurement to adjust a parameter of the other system.

Yet another feature of the present invention is a method in which the ellipsometer is used to calculate the optical constants of an opaque film to improve the model for calculating the film thickness using the photoacoustic system.

Yet another feature of the present invention is a method in which both the ellipsometer and photoacoustic system are used in the steps to measure, calculate and report the film thickness, the results of the measurements being combined to provide an improved result.

Yet another feature of the invention is a method in which both measurements of the ellipsometer and photoacoustic system are used to calculate the combined transparent and opaque thickness of a material film stack consisting of one or more transparent films lying over one or more opaque films.

Yet another feature of the invention is a method in which the ellipsometer is used to calculate the transparent film thickness, and the photoacoustic system is used to calculate the speed of sound in the film.

DESCRIPTION OF THE INVENTION

Figure 1:
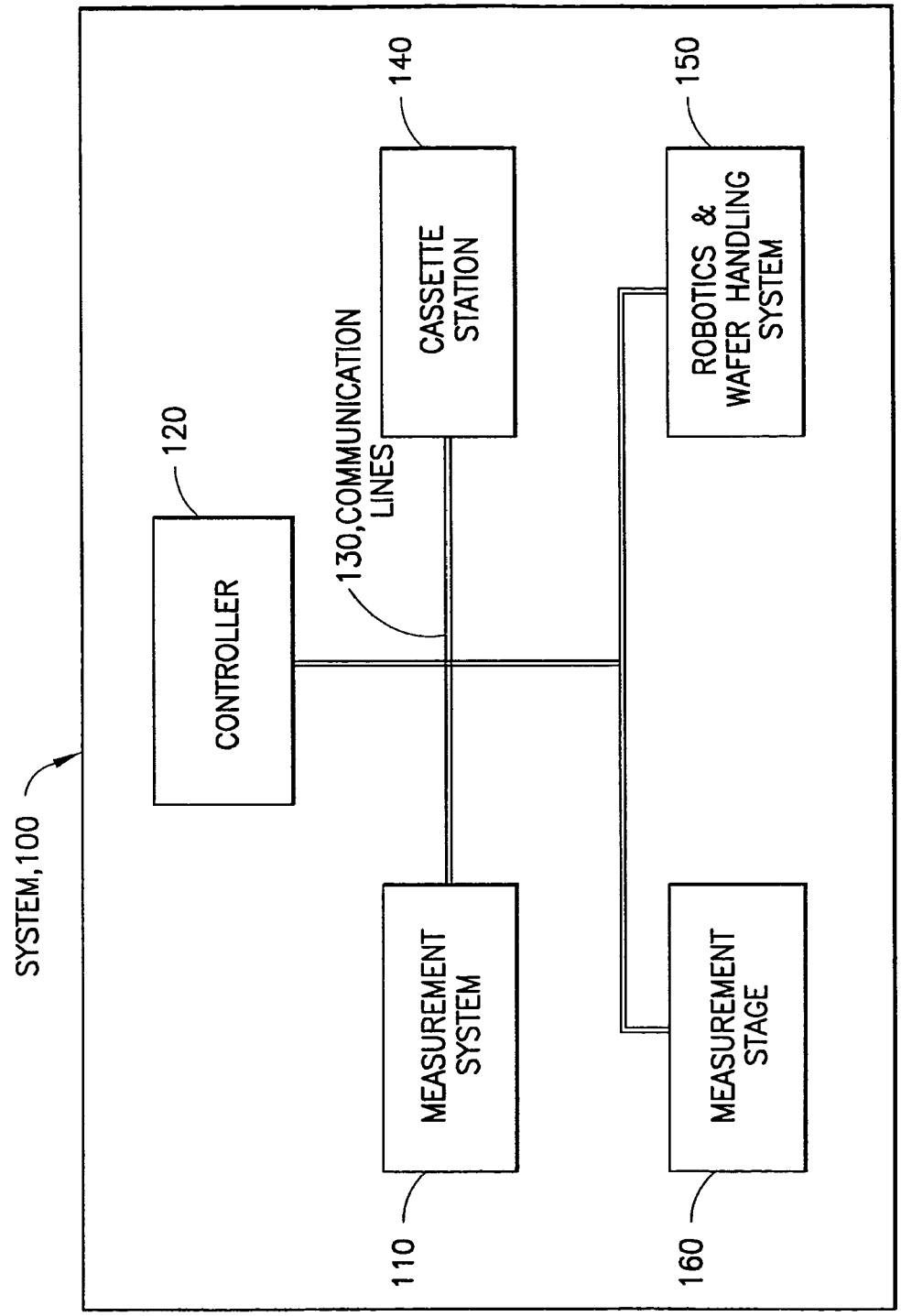
FIG. 1 illustrates schematically a prior art measurement system.

FIG. 1 shows a block diagram of a generalized prior art metrology system. Metrology system 100 comprises a measurement system 110, a controller 120, communication lines 130, a cassette station 140, a robotics & wafer handling system 150, and a measurement stage 160.

Measurement system 110 is either an ellipsometer or a photoacoustic system, as described in detail below. Measurement stage 160 comprises translation stages to position a wafer in a desired location beneath measurement system 110, and a translation stage to move the wafer toward or away from measurement system 110. Robotics and wafer handling system 150 comprises wafer gripping mechanisms, robots, and robotic controller system hardware and software to facilitate the transport of wafers from one location to another. Communication lines 130 are standard computer-to-instrument interface wires, fiber-optic cables, wireless, etc. Controller 120 comprises a computing device with a processor and memory. Controller 120 is electrically connected via communication lines 130 to measurement system 110, cassette station 140, robotics and wafer handling system 150, and measurement stage 160.

Figure 2:
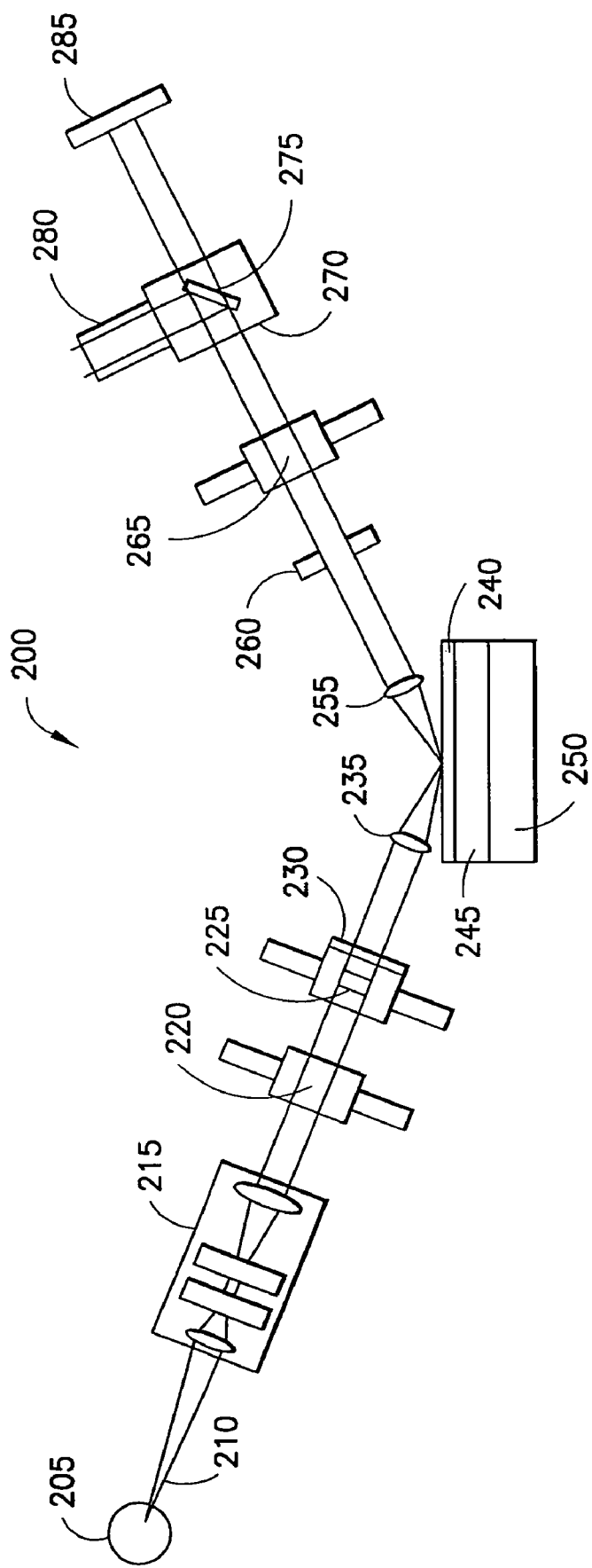
FIG. 2 illustrates a prior art ellipsometry system.

FIG. 2 shows the configuration of a typical prior art simultaneous multiple-angle spectroscopic ellipsometer. Ellipsometer 200 includes a light source 205 for generating a light beam 210, which passes through beam shaping optical system 215, polarizer 220, compensator 225, variable aperture 230 and first focusing lens 235. First focusing lens 235 directs light beam 210 onto film stack 240 on wafer 245 held by wafer stage 250. Light beam 210 reflects from film stack 240 and passes through second focusing lens 255, then through interchangeable aperture 260, analyzer 265 and into mirror box 270.

Beamsplitter 275 in mirror box 270 splits beam 210 into two beams, one that is directed to telescope 280 and another directed onto array detector 285.

Not all the components shown need be present in any particular instrument, and first and second focusing lens 235 and 255 may be compound lens systems. Lens 255 may also be eliminated from some systems.

The ellipsometer measures two parameters. The first is tan psi, the change in the amplitude ratio upon reflection. The second is delta, the change in the phase difference upon reflection of light beam 210. Psi and delta are functions of the optical constants of the surface, the wavelength of the light used, the angle of incidence, the optical constants of the ambient medium, and the thickness (t) and optical constants (n, k) of film stack 240.

In operation, tan psi and delta are measured at multiple incident angles theta, and the results compared to a theoretical model of the film or film stack being measured.

Figure 3:
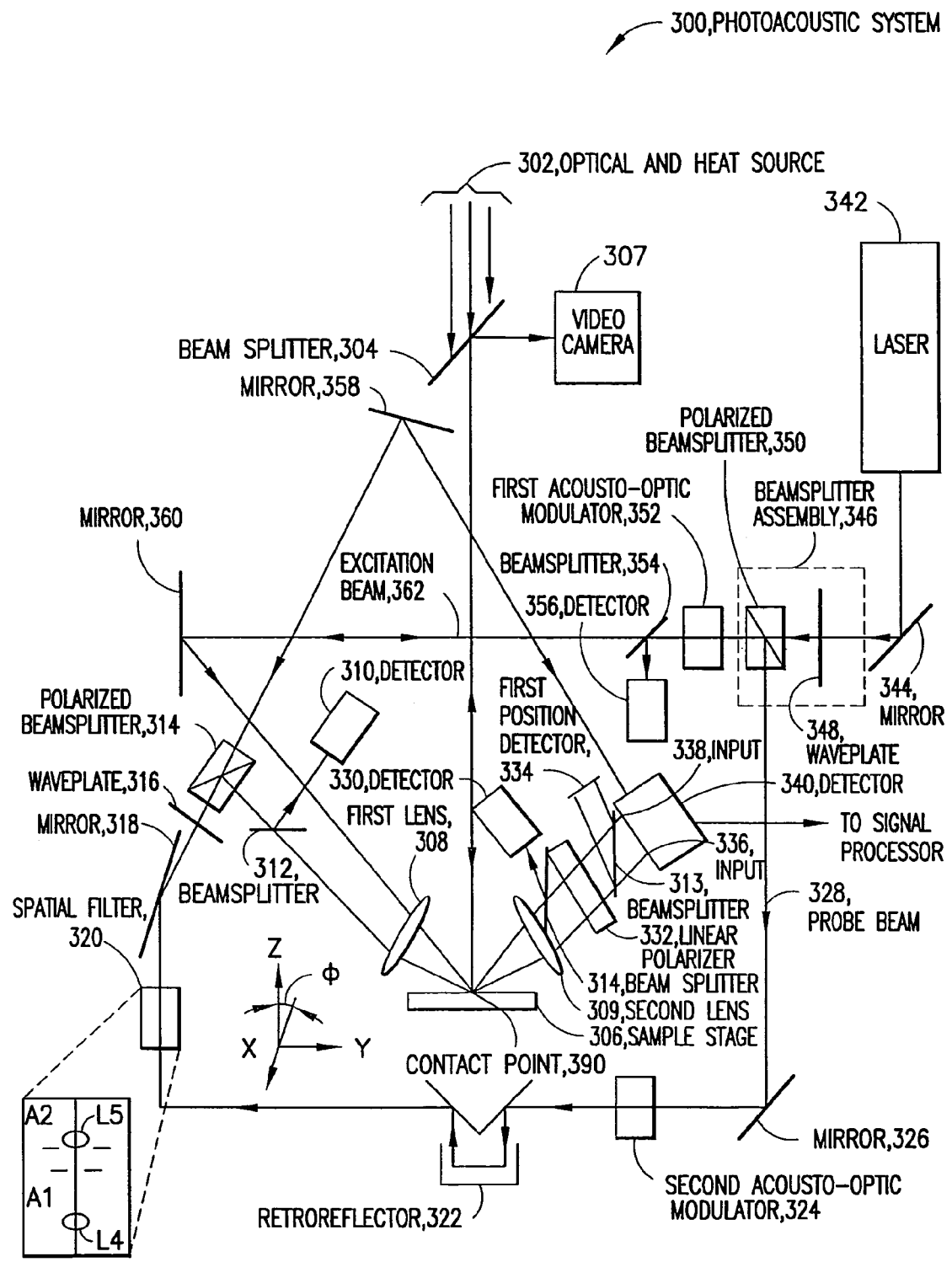
FIG. 3 illustrates schematically a prior art photo-acoustic measurement system.

FIG. 3 shows a configuration of a photoacoustic film thickness measurement system. Photoacoustic system 300 includes an optical/heat source 302 at the top of the Figure, a laser 342 at the top right, a video camera 307, a sample stage 306 at the top center, a mirror 360, a beam splitter 304 for directing radiation at the camera, a pump-probe beamsplitter assembly 346, a first acousto-optic modulator 352 adjacent to the beam-splitter assembly, and a second acousto-optic modulator 324 at the bottom right. Pump-probe beamsplitter assembly 346 includes a waveplate 348 and a polarized beamsplitter 350. Additionally photoacoustic system 300 includes a spatial filter 320 at the lower left, a retroreflector 322, a wave plate 316, a polarized beamsplitter 314 on the left, and a detector 340 with input 338.

Additionally photoacoustic system 300 includes a linear polarizer 332, a first lens 308, a second lens 309, a beamsplitter 313, a first position sensitive detector (PSD) 334, a detector 356, a beamsplitter 354, a beamsplitter 314 and a detector 330. Finally, the photoacoustic system 300 includes a detector 310 that is optically connected to beamsplitter 312 via sampled probe beam 328. These elements are interrelated as shown in FIG. 2.

Laser 342 is preferably a titanium-sapphire laser operating at 80 MHz and emitting light at a wavelength of 800 nm. The laser can also be configured with a frequency doubling crystal to emit light at 400 nm.

In operation, beamsplitter 312 is used to sample the intensity of the incident probe beam in combination with detector 310.

Additionally optical/heat source 302, which functions as a variable high-density illuminator, provides illumination for a video camera 307 and a sample heat source for temperature-dependent measurements under computer control. The video camera 307 provides a displayed image for an operator or appropriate pattern recognition software, and facilitates the setup of the measurement system.

The sample stage 306 is preferably a multiple-degree of freedom stage that is adjustable in height (z-axis), position (x and y-axes), and tilt (theta), and allows motor controlled positioning of a portion of the sample relative to the pump and probe beams. The z-axis is used to translate the sample vertically into the focus region of the pump and probe, the x- and y-axes translate the sample parallel to the focal plane, and the tilt axes adjust the orientation of the stage sample stage 306 to establish a desired angle of incidence for the probe beam.

Beam splitter 304 is a broadband beam splitter that directs video and a small amount of laser light to the video camera 307. The video camera 307 and local processor can be used to automatically position the pump and probe beams on a measurement site.

The pump-probe beam splitter assembly 346 splits an incident laser beam pulse (preferably of picosecond or shorter duration) into pump and probe beams, and includes a rotatable half-waveplate 348 that rotates the polarization of the incident beam. Waveplate 348 is used in combination with polarized beam splitter 350 to effect a continuously variable split between pump and probe power. This split may be controlled by the computer by means of a motor to achieve an optimal signal-to-noise ratio for a particular sample. The appropriate split depends upon factors such as the reflectivity and roughness of the sample. Adjustment is effected by having a motorized mount rotate waveplate 348 under computer control.

A first acousto-optic modulator 352 chops the pump beam at a frequency of about 1 MHz. A second acousto-optic modulator (AOM) 324 chops the probe beam at a frequency that differs by a small amount from that of the pump modulator acousto-optic modulator 352. As will be discussed below, the AOMs may be synchronized to a common clock source, and may further be synchronized to the pulse repetition rate (PRR) of the laser that generates the pump and probe beams.

A spatial filter 320 is used to preserve at its output a substantially invariant probe beam profile, diameter, and propagation direction for an input probe beam which may vary due to the action of the mechanical delay line shown as the retroreflector 322. The spatial filter 320 includes a pair of apertures A1 and A2, and a pair of lenses L4 and L5. An alternative embodiment of the spatial filter incorporates an optical fiber.

Waveplate 316 is a second adjustable half-waveplate that functions, with polarized beamsplitter 314, in a similar manner to the waveplate 348 and polarized beamsplitter 350 of the beamsplitter assembly 346. With waveplate 316, the intent is to vary the ratio of the part of the probe beam impinging on the sample to that of the portion of the beam used as a reference (input to input 338 of detector 340). Waveplate 316 may be motor controlled to achieve a ratio of approximately unity. The electrical signals produced by the beams are subtracted, leaving only the modulated part of the probe to be amplified and processed. The linear polarizer 332 is employed to block scattered pump light polarization, and to pass the probe beam. First and second lenses 308 and 309 are pump and probe beam focusing and collimating objectives, respectively. The beamsplitter 313 is used to direct a small part of the pump and probe beams onto a first position sensitive detector 334 that is used for auto focusing, in conjunction with the processor and movements of the sample stage 306. The position sensitive detector 334 is employed in combination with the processor and the computer-controlled sample stage 306 (tilt and z-axis) to automatically focus the pump and probe beams onto the sample to achieve a desired focusing condition.

A dual metrology system is described below.

Figure 4:
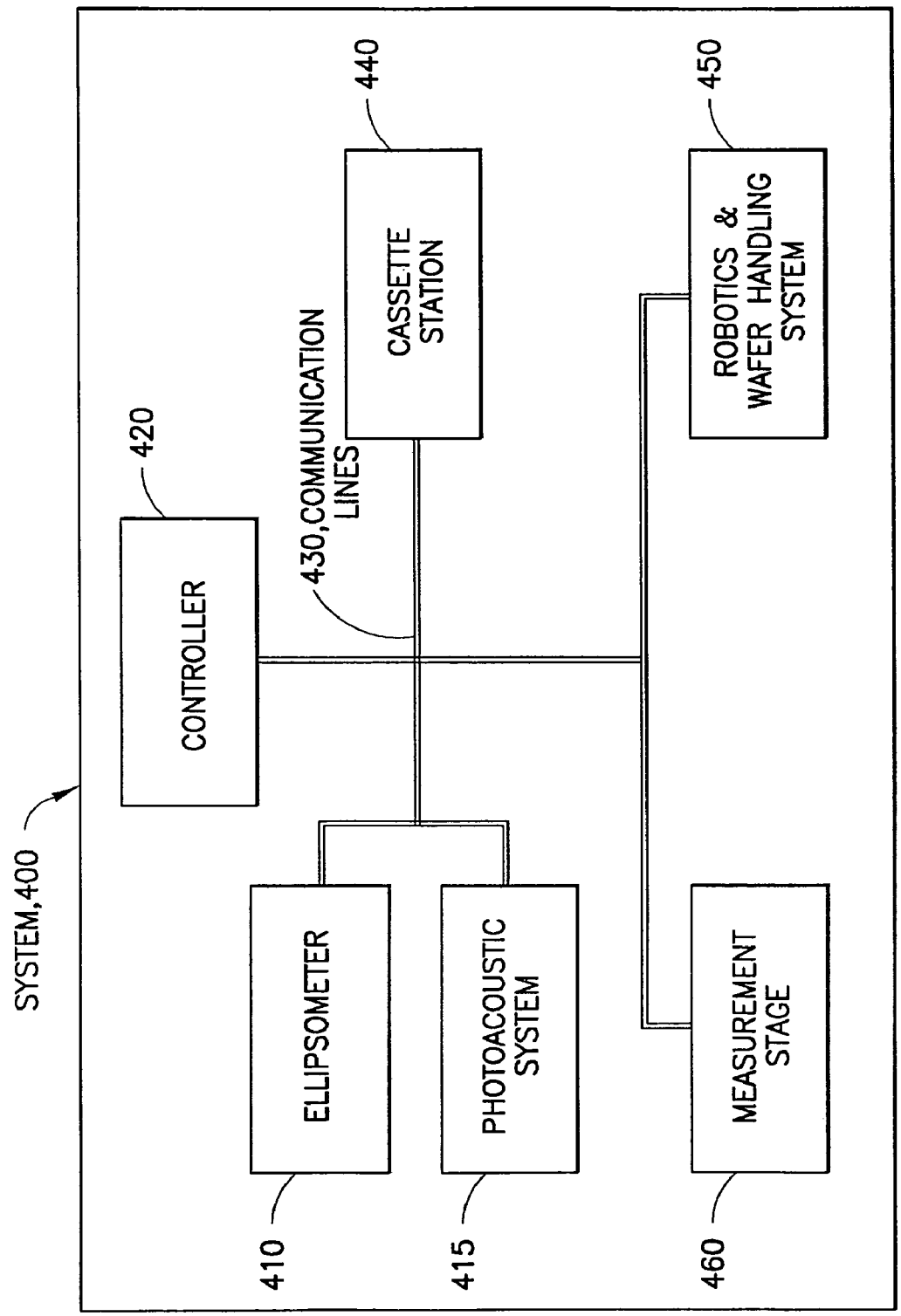
FIG. 4 illustrates schematically a measurement system according to the invention.

FIG. 4 illustrates a plan view of a dual measurement system for measuring the thickness of transparent and opaque films by combining a spectroscopic ellipsometer 410 and a photoacoustic thickness system 415. Sharing the laser provides for a substantial reduction in cost.

Figure 5:
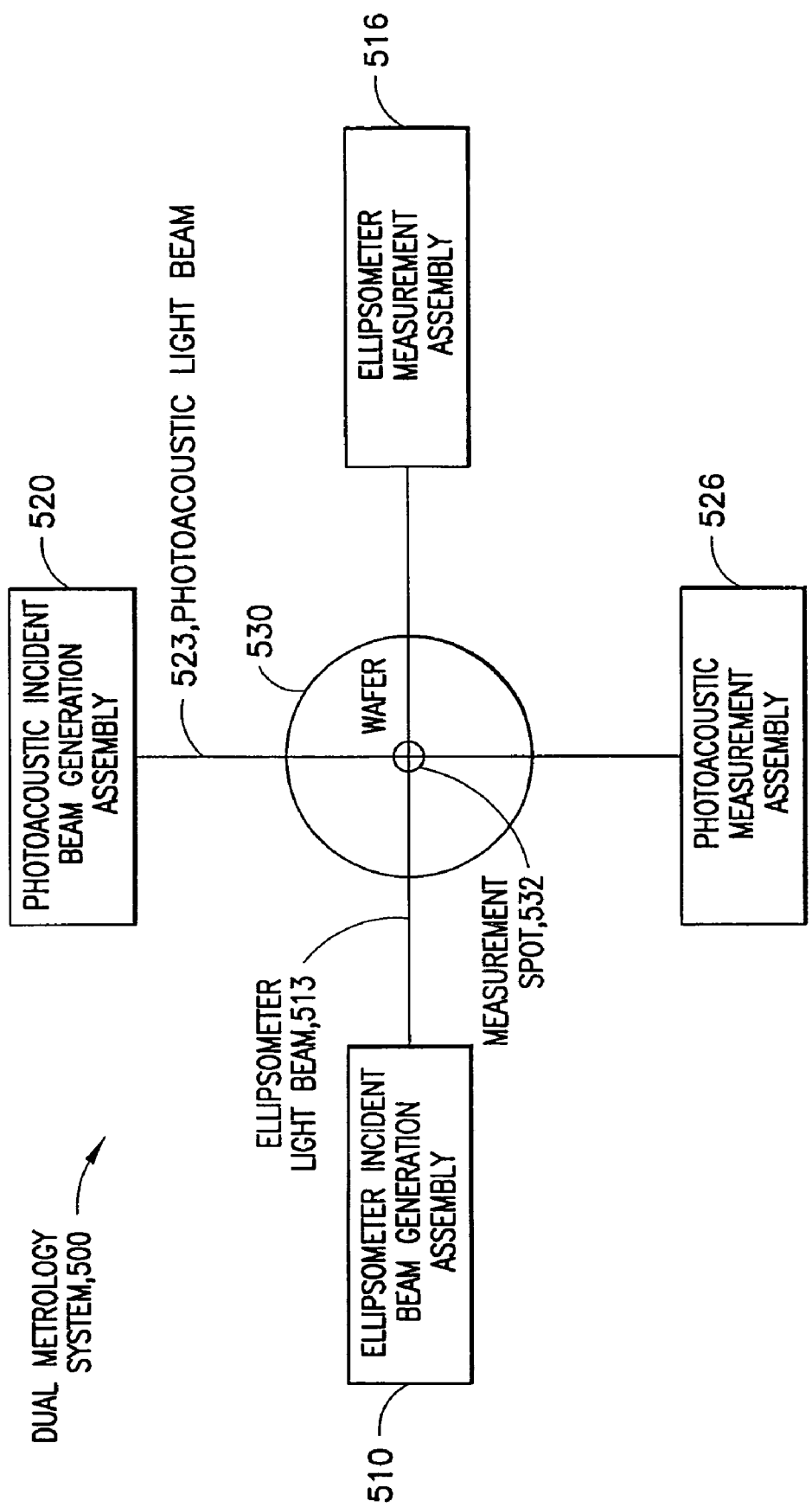
FIG. 5 illustrates a plan view of a measurement system according to the invention.

FIG. 5 shows a plan view of a dual metrology system including a spectroscopic ellipsometer and a photoacoustic film thickness measurement system arranged transversely to one another. Dual metrology system 500 comprises ellipsometer incident beam generation assembly 510, ellipsometer measurement assembly 516, photoacoustic incident beam generation assembly 520 and photoacoustic measurement assembly 526.

With regard to the ellipsometer, the correspondences between FIG. 5 and FIG. 2 are as follows. Ellipsometer incident beam generation assembly 510 corresponds to 205, 215, 220, 225, 230 and 235; ellipsometer measurement assembly 516 corresponds to 255, 260, 265, 270, 275, 280 and 285; ellipsometer light beam 513 corresponds to light beam 210; and wafer 530 corresponds to 240 and 245.

With regard to the photoacoustic system, the correspondences between FIG. 5 and FIG. 3 are as follows. Photoacoustic incident beam generation assembly 520 corresponds to all elements in the optical path from sample stage 306 and laser 342 via first lens 308; photoacoustic light beam 523 corresponds to excitation beam 362; wafer 530 is not shown in FIG. 3, but is normally placed on sample stage 306; and photoacoustic measurement system 526 corresponds to the collection of all other elements and assemblies in FIG. 3.

Figure 6:
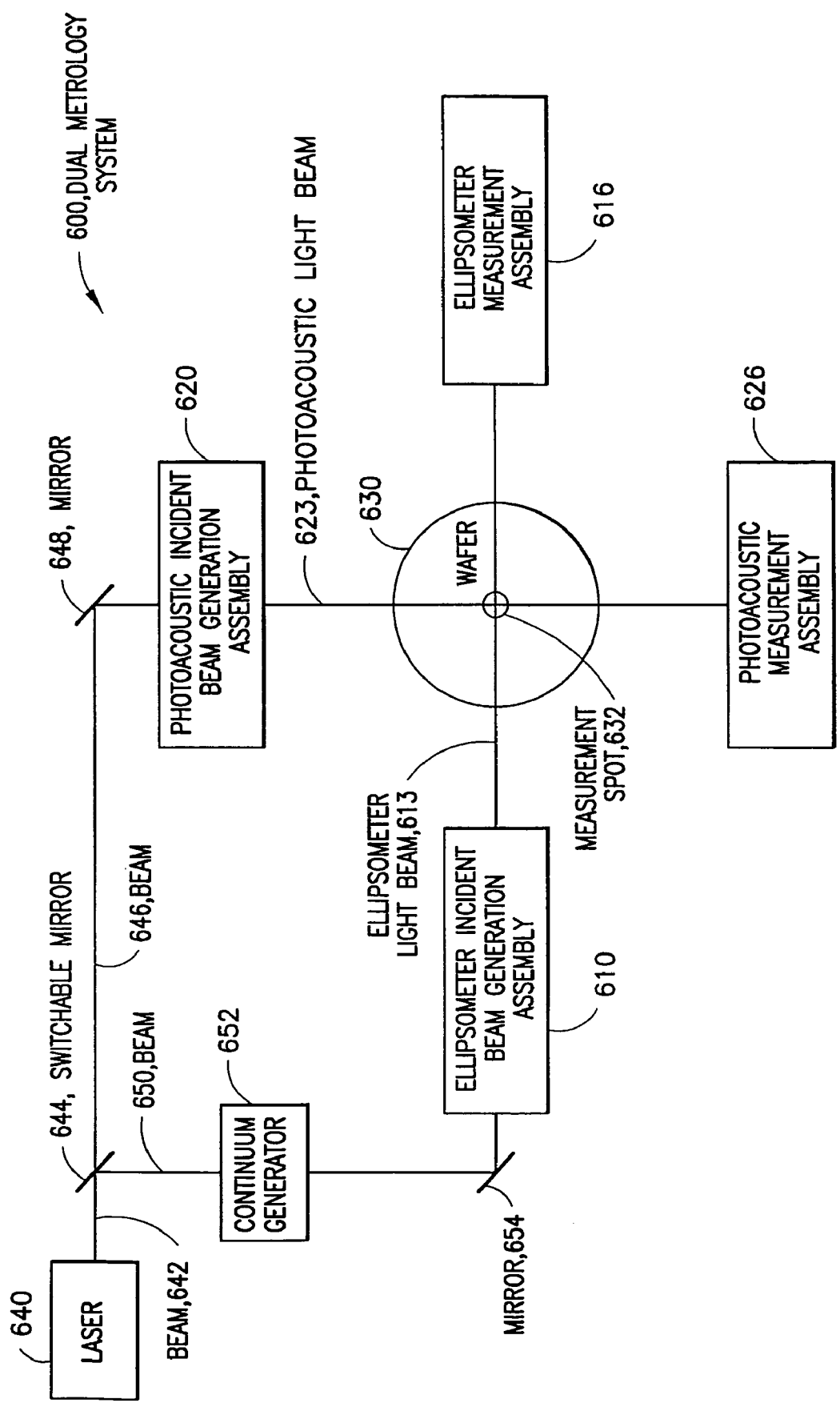
FIG. 6 illustrates a plan view of an alternative embodiment of a measurement system according to the invention.

FIG. 6 shows an alternative embodiment of a dual metrology system wherein ellipsometer incident beam generation assembly 610 and photoacoustic incident beam generation assembly 620 are supplied light from the same laser 640. All elements and assemblies in the range of 610 to 630 in FIG. 6 are respectively identical to 510 to 530 in FIG. 5.

Figure 8:
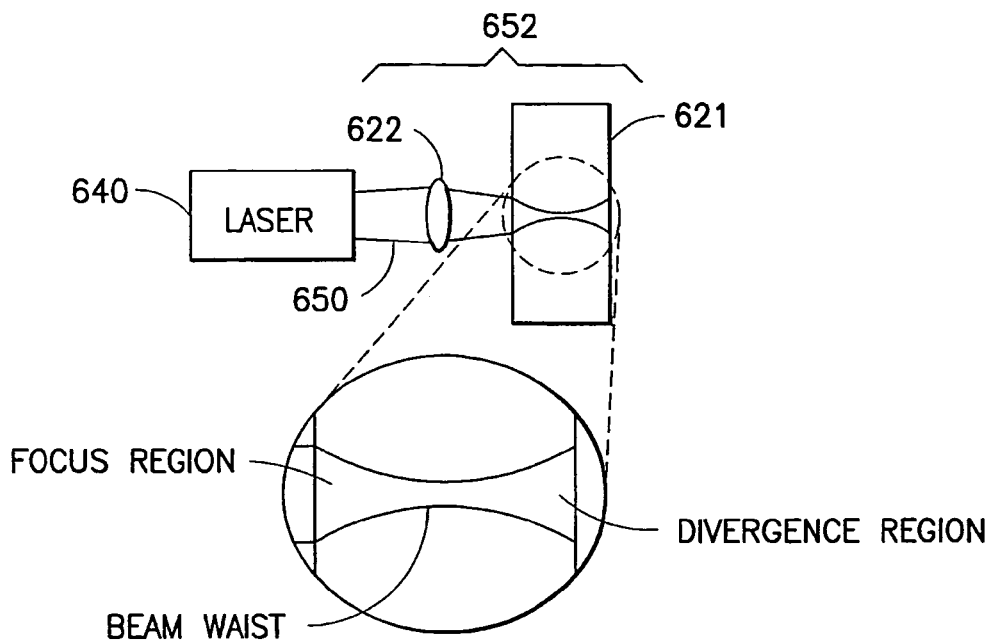
FIG. 8 illustrates a broadband component of an ellipsometer.
Figure 9:
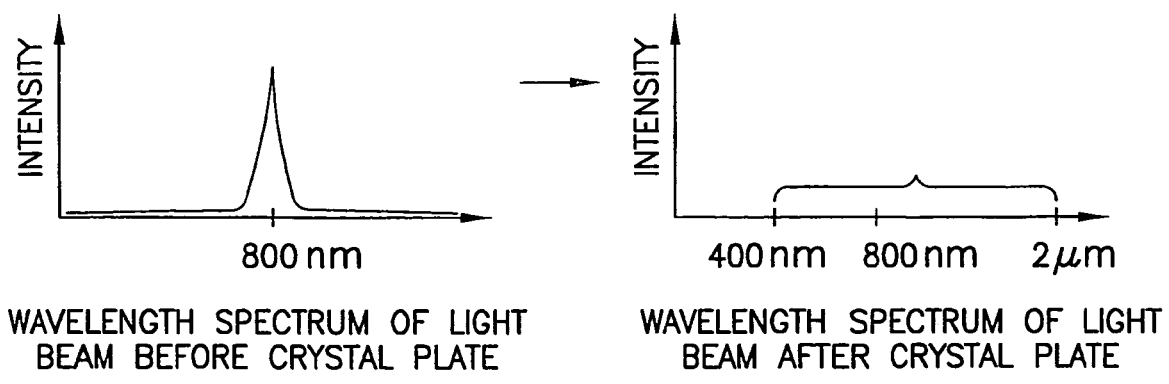
FIG. 9 illustrates a broadband spectrum for an ellipsometer.

The dual metrology system 600 in FIG. 6 additionally includes a laser 640, switchable mirror (or beam splitter) 644, mirror 648, continuum generator 652, and mirror 654. The beam 642 exiting from laser 640 becomes either beam 646 or 650, depending on the operation of switchable mirror 644. Beam 646 is directed via mirror 648 to photoacoustic incident beam generation assembly 620, and beam 650 is directed via continuum generator 652 and mirror 654 to ellipsometer incident beam generation assembly 610. Thereby, both ellipsometer incident beam generation assembly 610 and photoacoustic incident beam generation assembly 620 are supplied laser light by the same laser light source, i.e., laser 640. The continuum generator 652 in FIG. 6 generates a continuum from laser 640 so that the beam waist of beam 650 is reduced, thereby reducing the spot size of ellipsometer light beam 613 when it strikes the measurement spot 632 on wafer 630. In a first embodiment, the continuum is generated by a continuum generator that comprises a lens 622 in FIG. 8 that focuses the beam on a crystal 621, e.g. sapphire, that generates a broad frequency spectrum. FIG. 9 shows the spectrum of the beam before and after crystal plate 621, converting a narrowband incident beam peaked at 800 nm to a broadband beam having an intensity distribution substantially uniform from 400 nm through 2 microns. In one embodiment, a sapphire plate reduced the beam spot size to less than 3 microns is diameter.

The problem addressed by the continuum generator is that ultrafast femtosecond pulse lasers in the microjoule power range used in multiple-angle spectroscopic ellipsometers generate a beam having a low peak power. Those skilled in the art well appreciate that this low peak power results in a poor signal to noise ratio. According to one aspect of the present invention, the beam spectrum is broadened, such that the spot size on the target is reduced in diameter and the beam intensity is increased, without increasing the power of the laser. Advantageously, the decrease in beam spot size permits the measurement of smaller geometries.

Since the continuum generator 652 in the present embodiment makes beam 650 a microspot broadband beam, without otherwise affecting operation, continuum generator 652 is optional and could be omitted if the intensity in a conventional beam is acceptable.

In another embodiment of the combined system, continuum generator 652 incorporates a short length of commercially available photonic crystal optical fiber. The purpose of the fiber is to generate a high-brightness broadband continuum from laser 640. A lens focuses the laser beam 650 onto the input face of the fiber. The continuum output is directed to the ellipsometer incident beam generation assembly 610 and produces a single mode output with beam waist defined by the mode field diameter of the fiber.

In yet another embodiment of the combined system, continuum generator 652 incorporates a short length of commercially available tapered optical fiber. The fiber is tapered such that the diameter is reduced to a few microns along the central portion of its length. The tapered region of the fiber will exhibit highly non-linear optical properties and will generate a high-brightness broadband continuum from laser 640. A lens focuses the laser beam 650 onto the input face of the fiber. The continuum output is directed to the ellipsometer incident beam generation assembly 610 and produces a single mode output with beam waist defined by the mode diameter of the fiber.

In yet another embodiment of the present invention, ellipsometer 410 of dual metrology system 400 can also be any other type of transparent film thickness measurement system, such as a reflectometer.

Method of Operation

The method for measuring the thickness of a film on a wafer using the dual metrology system is described below.

Figure 7:
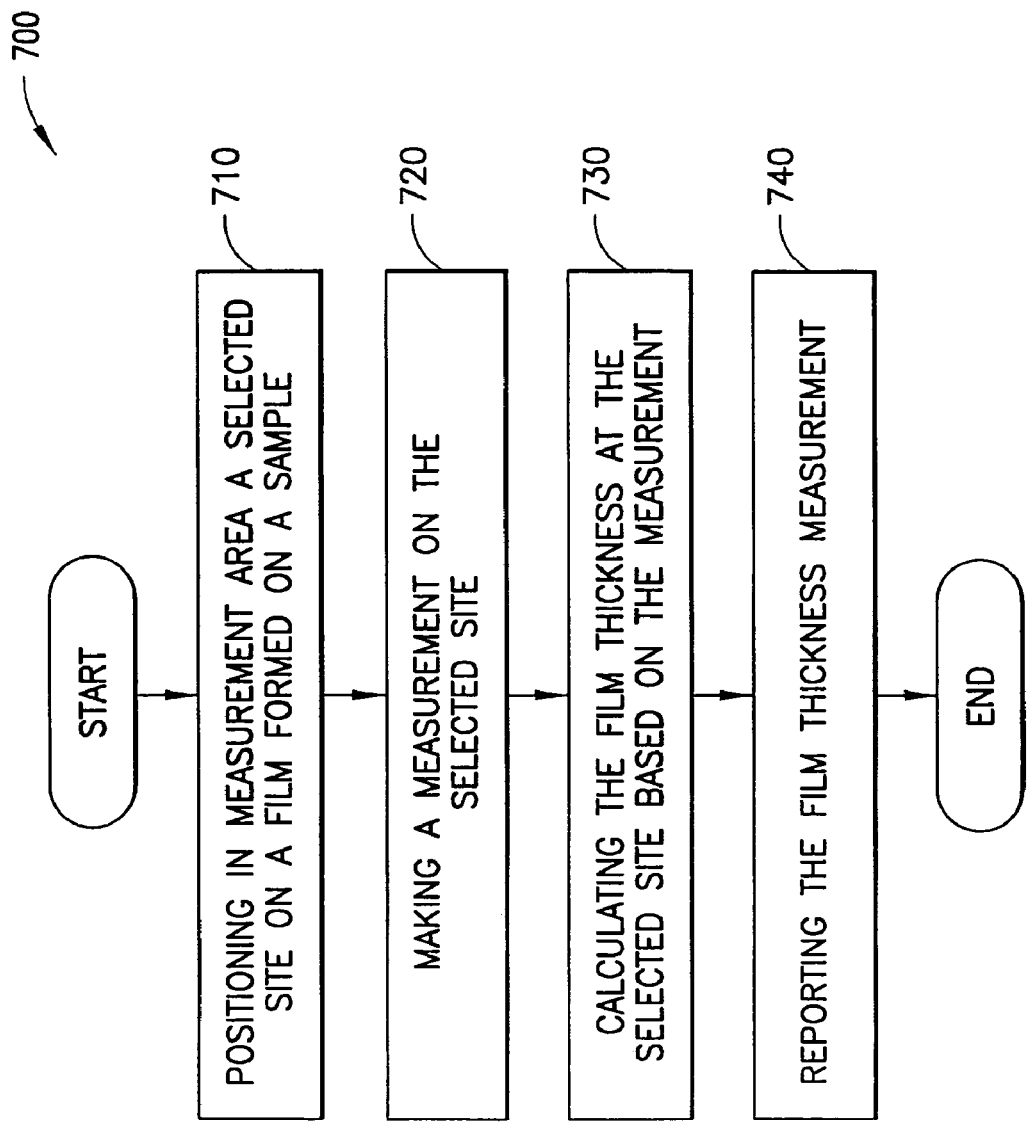
FIG. 7 illustrates steps in a method of a measurement according to the invention.

FIG. 7 is a flowchart of a method of measuring the thickness of a film on a wafer using the dual metrology system. Method 700 includes the following steps:

Step 710: Positioning in Measurement Area a Selected Site on a Film Formed on a Sample In this step, controller 420 sends an instruction via communication lines 430 to robotics & wafer handling system 450 to load a wafer from cassette station 440 onto measurement stage 460 and to position the wafer such that the site is located in the focal area.

Step 720: Making a Measurement on the Selected Site

In this step, controller 420 sends an instruction via communication lines 430 to either ellipsometer 410 or photoacoustic system 415, depending on whether the film to be measured on the wafer is respectively transparent or opaque, to make a measurement at the selected site.

Step 730: Calculating the Film Thickness at the Selected Site Based on the Measurement In this step, controller 420 (or either ellipsometer 410 or photoacoustic system 415) calculates the film thickness at the selected site based on the measurement made in step (b). The calculation can be performed in any unit that is convenient. The ellipsometer or photo-acoustic system may or may not include a unit with calculation capability, as the designer prefers.

Step 740: Reporting the Film Thickness Measurement

In this step, either ellipsometer 410 or photoacoustic system 415 reports the measurement of the film thickness.

In an alternative method of operation, both ellipsometer 410 and photoacoustic system 415 are used in steps 720, 730 and 740 to measure, calculate and report the film thickness (refer to FIG. 6). The results of both measurements are then used, for example, to calculate the combined transparent and opaque thicknesses. Further, ellipsometer 410 can be used to calculate the transparent film thickness, and photoacoustic system 415 can be used to calculate the speed of sound in the film. Further, ellipsometer 410 can be used to calculate the "optical constants" meaning, as used in the field, n (refractive index) and k (absorption coefficient) of an opaque film to improve the model for calculating the film thickness using photoacoustic system 415. Further, ellipsometer 410 can be used to calculate the transparent film thickness, and that result can be used to improve the model for calculating the density of the film using photoacoustic system 415.

In one embodiment of the invention, both the ellipsometer and photoacoustic system are used to measure, calculate and report the film thickness. The two results may be combined to give an improved value for thickness by calculating a weighted average of the results, the weight depending on the designed thickness of the film.

In another embodiment of the invention, both measurements of the ellipsometer and photoacoustic system are used to calculate the combined transparent and opaque thicknesses of a material film stack consisting of one or more transparent films lying over one or more opaque films. For example, the photoacoustic system would measure the total thickness of a film stack. The ellipsometer would measure the thickness of the upper transparent layer(s). Subtraction gives the thickness of the opaque layers.

In another embodiment, the ellipsometer is used to calculate the transparent film thickness, and the thickness measurement from the photoacoustic system is used to calculate the speed of sound in the film. Measurement of the speed of sound provides information about the material hardness under elastic deformation.

In general, a thickness measurement is the product of a formula containing several parameters that may be of interest; e.g. hardness, doping level, stoichiometry, etc. Ordinarily, the operator will plug in handbook values for various parameters. With a system according to the invention, it is possible to combine two measurements to find a parameter representing the actual film being measured.

In the case of a fabrication process using damascene technology, in which a trench is etched in a dielectric, the trench is filled with metal and the excess metal is removed by chemical-mechanical polishing, there may be excess metal removed from the trenches in some locations and/or excess dielectric removed in areas between concentrations of metal. The photoacoustic system may be used to measure the metal thickness and the ellipsometer may be used to measure the thickness of the dielectric (commonly oxide). The thicknesses (or their ratio) may be measured across the wafer for quality control. In another embodiment, the ellipsometer is used to calculate the optical constants of an opaque film to improve the model for calculating the film thickness using the photoacoustic system. The actual values (n,k) for the particular film being measured are used by the photoacoustic system, giving a better fit to the data than handbook values that would otherwise be used.

In another embodiment, the ellipsometer is used to calculate the transparent film thickness, and that result is used, as in the previous paragraph, to improve the model for calculating the density of the film using the photoacoustic system. The photoacoustic measurement depends on the sound velocity and density for each film. Since the sound velocity and density may both depend on the same process parameters, the use of ellipsometer results allows a velocity calculation with the photoacoustic data. This velocity can then be used for the density calculation.

If the spectroscopic ellipsometer employed in the dual metrology system is a microspot broadband spectroscopic ellipsometer, the noise level of the continuum generation could potentially reduce the signal-to-noise ratio, thus affecting measurement accuracy. However, this could be overcome by using a higher power light source, such as by using a power amplifier in the laser to boost the pulse energy of the light beam.

Another advantage of the invention is that both the ellipsometer and photoacoustic system may be used to measure, calculate and report the film thickness. For example, this technique may be particularly useful for the case of thin or semi-transparent films. Such films may be relatively thin, and thus more transparent, at some locations on a sample and thicker at other locations. The calculated thickness at any site may be derived from a weighted combination of thickness measurements from both the ellipsometry and photoacoustic systems. Reported thickness at thinner or more transparent sites may tend to rely more heavily on the ellipsometry result, while thicker sites may rely more heavily on the photoacoustic result.

In the following claims, the term "calculating" means any of using a general-purpose computer to operate on measured values generated by the ellipsometer and/or the pa, or using an arithmetic controller or computer incorporated in one or both of the measurement systems.

Although the invention has been described with respect to a limited number of embodiments, those skilled in the art will appreciate that other embodiments may be constructed within the spirit and scope of the following claims.

The invention claimed is:

1. A method of manufacturing a semiconductor device using a damascene process comprising:
   selecting a site on a semiconductor substrate for measurement of a damascene structure formed on the substrate, where the damascene structure comprises at least one metal filled trench formed into the substrate and the trench is bounded on at least one side by a dielectric material;
   using one of an ellipsometer and a photoacoustic system to measure a value of a first parameter of the damascene structure at the selected site;
   using the other of the ellipsometer and the photoacoustic system to measure a value of a second parameter of the damascene structure at the selected site; and
   calculating an output parameter based at least in part on the first and second parameters, where the output parameter is correlated to a physical characteristic of the damascene structure of the substrate that has been modified by a polishing process.

2. The method of claim 1 wherein the output parameter is a thickness of one of the at least one metal filled trench formed into the substrate.

3. The method of claim 1 wherein the output parameter is a thickness of the dielectric material.

4. The method of claim 1, wherein the output parameter is indicative of a variation between a thickness of one of the at least one metal filled trench and a thickness of the dielectric material.

5. The method of claim 1, wherein the output parameter is a ratio of the thicknesses of one of the at least one metal filled trench and the dielectric material.

6. The method of claim 1, wherein the ellipsometer is used to measure a parameter of the dielectric material and the photoacoustic system is used to measure a parameter of one of the at least one metal filled trench.

7. The method of claim 1, wherein the ellipsometer is used to measure a parameter of one of the at least one metal filled trench and the photoacoustic system is used to measure the same parameter of the metal filled trench, the two values of the parameter of the one of the at least one metal filled trench being combined to obtain an improved parameter value.

8. The method of claim 7, wherein the two parameter values comprise a weighted average.

9. The method of claim 1, further comprising obtaining, using at least one of the ellipsometer and the photoacoustic system, at least one parameter of a film stack of which the damascene structure forms a part and calculating a difference between the at least one parameter and the output parameter, the difference correlating to a relationship between the physical characteristic of the damascene structure and a physical characteristic of one of the at least one metal filled trench.

10. The method of claim 9, wherein the physical characteristic of the damascene structure is a thickness and the physical characteristic of the film stack is a thickness.

11. The method of claim 1, further comprising modifying the polishing process based at least in part on the output parameter.

12. The method of claim 11, further comprising:
calculating a ratio between the output parameter and the at least one parameter, the ratio being indicative of a cumulative action of the polishing process on the film stack; and
modifying the polishing process based at least in part on the ratio.

13. The method of claim 11, where the polishing process is a chemical-mechanical polishing process.

14. The method of claim 1, where using the other of the ellipsometer and the photoacoustic system further comprises measuring a value of a second at least one additional parameter.

15. The method of claim 1, where using one of an ellipsometer and a photoacoustic system further comprises measuring a value of a first at least one additional parameter.

16. A semiconductor device fabricated according to the method of claim 1.

* * * * *